United States Patent [19]

November et al.

[11] Patent Number: 4,899,576

[45] Date of Patent: Feb. 13, 1990

[54] METHOD FOR TESTING REPEATABILITY OF A RHEOLOGIC SYSTEM

[75] Inventors: Daniel November, New York, N.Y.;
William E. Langley, Lodi, N.J.;
Harry Darnopuk, Brooklyn, N.Y.;
George V. Hectus, Verona, N.J.

[73] Assignee: Haake-Fisons Instruments, Inc., Saddle Brook, N.J.

[21] Appl. No.: 297,989

[22] Filed: Jan. 17, 1989

Related U.S. Application Data

[63] Continuation-in-part of Ser. No. 88,404, Aug. 24, 1987, abandoned, which is a continuation-in-part of Ser. No. 917,619, Oct. 19, 1986, abandoned.

[51] Int. Cl.[4] .............................................. G01N 11/14
[52] U.S. Cl. .............................................. 73/59; 73/54
[58] Field of Search ...................... 73/59, 60, 54, 1 C, 73/862.04, 862.35

[56] References Cited

U.S. PATENT DOCUMENTS

| | | | |
|---|---|---|---|
| 2,927,457 | 3/1960 | Pye et al. | 73/59 |
| 3,285,075 | 11/1966 | De Zurik | 73/59 |
| 4,077,251 | 3/1978 | Winter | 73/59 |
| 4,171,647 | 10/1979 | Herrgen | 73/1 C |
| 4,299,119 | 11/1981 | Fitzgerald et al. | 73/59 |
| 4,352,287 | 10/1982 | Orth et al. | 73/60 |
| 4,594,883 | 6/1986 | Pollard | 73/54 |
| 4,706,506 | 11/1987 | Lestelle | 73/862.35 |

FOREIGN PATENT DOCUMENTS 126297 9/1945 Australia .......................... 73/862.35

Primary Examiner—Hezron E. Williams
Attorney, Agent, or Firm—M. K. Silverman

[57] ABSTRACT

A method for testing the repeatability of test runs of a rheologic instrument. Such instrument will, typically, include a power shaft and a test chamber. The disclosed method constitutes the step of using a torque transducer to reiteratively compare the reactive torques imparted to a power shaft through the use of sequences of rheologic references.

7 Claims, 3 Drawing Sheets

METHOD FOR TESTING REPEATABILITY OF A RHEOLOGIC SYSTEM

REFERENCE TO RELATED APPLICATION

This case is a continuation-in-part of application Ser. No. 07/088,404, filed Aug. 24, 1987, now abandoned, which is a continuation-in-part of application Ser. No. 06/917,619 filed Oct. 19, 1986, now abandoned.

BACKGROUND OF THE INVENTION

Many analytical laboratory instruments make use of a propellor and power shaft to generate internal pressures, densities, torques and forces, all of which, directly or indirectly influence the viscosity of the liquid phase of the test material. Examples of this type of physical phenomenon which may be measured or determined through rheological measuring procedures are the following: flow rate of polymers, surface properties, air bubble entrapment, fiber wetout, and structural integrity of the test sample.

The present inventive method makes usage of a strain transducer. Strain transducers, as such, have long been known in the prior art. However, their usage in the method as set forth herein is believed to be novel.

The most related prior art of which the invention are aware comprises U.S. Pat. No. 3,285,057 (1966) to De Zurik; No. 4,171,647 (1979) to Herrgen; No. 4,445,365 to Jelby; No. 4,352,287 to Orth; No. 4,445,365 (1984) to Selby; No. 4,706,506 (1987) to Lestelle; and United Kingdom Patent No. 1,181,961 (1970) to Brooking.

The above and other prior art are not capable of measuring or responding to all components of torque which are torsionally imparted to the power shaft within the test vessel. More particularly, the prior art does not teach a test method which measures or utilizes both the radial and axial components of torque in the test vessel. The present invention advantageously employs these torque components as a part of an effective test method.

SUMMARY OF THE INVENTION

The invention constitutes a method for testing the torque parameter repeatability of test runs of a rheological measuring system, said system having a power shaft and a test chamber, the method comprising the steps of: providing a circumferential mixing element for said power shaft in said test chamber; and orienting a transducer within a spiral segment of a curved plane of rotation of said power shaft, said plane corresponding to the dynamic curvature of said mixing element of said power shaft, to reiteratively compare the integrated axial and radial reactive torques imparted to said mixing element through the use of rheologic reference material samples for comparing the reactive torques thereof, whereby, reactive torques, both axial and radial, will be transmitted through the power shaft of said transducer and, further whereby, differences in the comparative reactive torques will indicate a lack of repeatability in sequential test runs of the system.

It is an object of the present invention to provide a method and means for testing the repeatability of the output of a rheological measurement instrument.

It is another object to provide a method and means for simply, conveniently, and cost-effectively determining the repeatability and, thereby, correctness of calibration of a test instrument employing a power shaft as an element thereof.

It is a further object to provide a method for testing the repeatability of the output of instruments employed in measuring the viscosity of the liquid phase of normally solid materials such as polymers.

It is a yet further object to provide a quality control means for the testing of analytic instruments prior to their use in an applied engineering environment, such as an extrusion system.

The above and yet further objects and advantages of the present invention will become apparent from the hereinafter set forth Detailed Description of the Invention, the Drawings, and Claims appended herewith.

DETAILED DESCRIPTION OF THE INVENTION

It is well known in the prior art to make use of so-called torque rheometers (which may be subject to microprocessor control) to measure the rheological properties of the liquid phase of a resin, such properties including, for example, viscosity, material uniformity and air bubble entrapment. However, in such rheologic measuring systems, it is important to insure repeatability of the test data when the same resins, or other test materials, are provided to mixing apparatus 8 and its test chambers 12 under similar conditions of torque from power shaft 10, temperature and pressure within the test chamber 12, and other variables that are a part of the formulation in the preparation of a resin or the like, prior to an extrusion, injection molding or other processes.

Accordingly, it is of considerable importance to insure that the rheological measuring equipment is working in a precisely repeatable fashion before use thereof is made. In this sense, the present inventive method may be viewed as a method for testing or calibrating an analytic test system.

Figure 1:
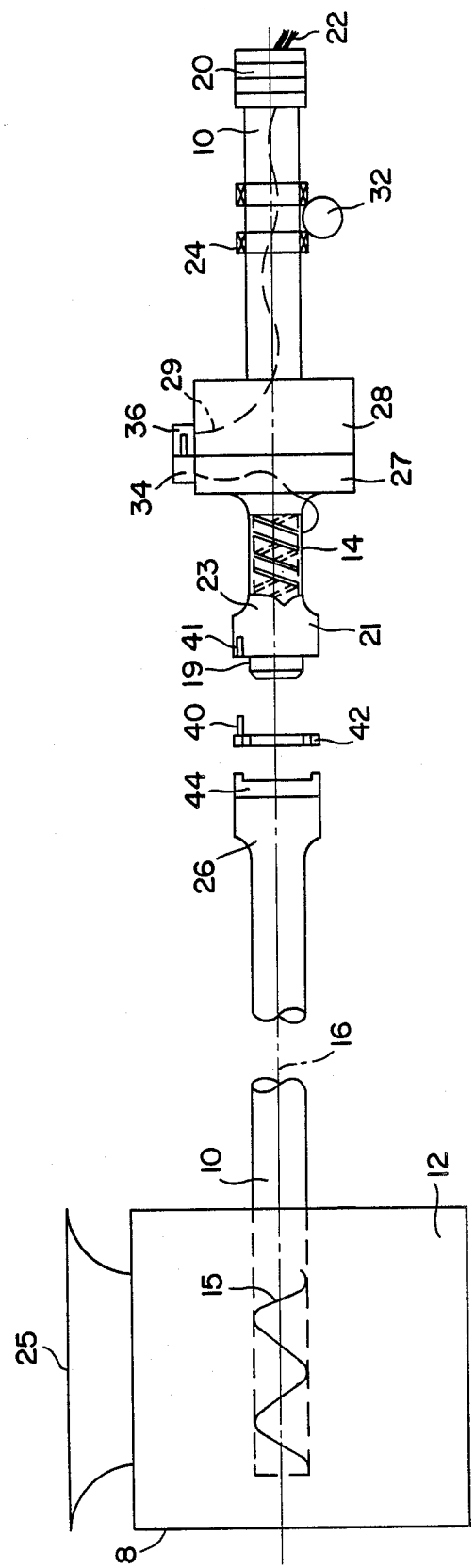
FIG. 1 is a diagrammatic exploded view of the inventive system and its related environment.

With reference to FIG. 1 and, more particularly, the left-hand side thereof, there is shown the mixing apparatus 8 which includes the test chamber 12, a hopper 25, the power shaft 10, and a spiral mixing element 15 by which resin pellets or other test materials are selectively dropped into hopper 25 for purposes of mixing within test chamber 12 by virtue of the rotation of the said mixing element.

Typically, such mixing occurs at a pre-determined temperature. Such mixing will generate values from mixing elements 15 and thru power shaft 10. This torque may be considered in terms of axial and radial components which are imparted to the lattice structure of the material placed into chamber 12. In many applications, said pellets are elevated in temperature such that the resin, or other test material, is in its liquid phase during the interval of rotation of power shaft 10 and the mixing element 15.

With further reference to FIG. 1, it is to be appreciated that the use of the spiral (or screw-like) mixing element 15 accomplishes, by virtue of its special geometry, a summing of the axial and radial components of the reactive torque imparted from the test material. This reactive torque is then torsionally transmitted to a spirally-wound transducer 14 (further described below).

In FIG. 1, power shaft 10 is provided with an output coupling 26. To said output coupling 26, and in alignment with the axis of rotation 16 of power shaft 10, is provided a driver coupling plate 44. This element is, in turn, mechanically mated to a driver coupling plate 42 which includes a shear pin 40. Said coupling plate 42 is axially secured to male element 21 through key 19 and shear pinhole 41 (See also FIG. 3). Male element 21 is integral with linkage 23, about which is spirally-wound said transducer means 14 which, in a preferred embodiment, is a torsional strain gauge in the nature of a piezoelectric element. A piezoelelectric element, by definition, generates an analog electrical output as a direct and, within a given range, linear output of an input of mechanical pressure. In the instant application, the input is in the nature of a spiral torque torsionally imparted to transducer 14 from spiral mixing element 15 through the rotation of power shaft 10 in test chamber 12.

Accordingly, it may be appreciated that the winding pattern of the strain gauge transducer 14 which is wound upon a spiral segment of a curved plane of rotation of power shaft 10, will thereby define a geometry corresponding to the dynamic curvature of the mixing element of the shaft, i.e., the geometry defined by the mixing element when it is rotated and, further, there will be transmitted through the power shaft to the transducer 14 a so-called integrated axial and radial reactive torque, that is, a reactive torque summing both the axial and radial components thereof.

The positioning of transducer 14, in the above manner, is significant in that it will serve to measure the integrated total of the axial and radial components of reactive torque from the test sample imparted to the mixing element 15 and power shaft 10. Thereby, when the output of the transducer 14 is compared with rheologic reference standards an accurate determination can be made as to whether the torque rheometer system is operating properly.

In that the curvature of the winding of strain gauge transducer 14 follows the dynamic geometry of mixing element 15, both the axial and radial components of the reactive torques from the test material are faithfully measured.

Figure 3:
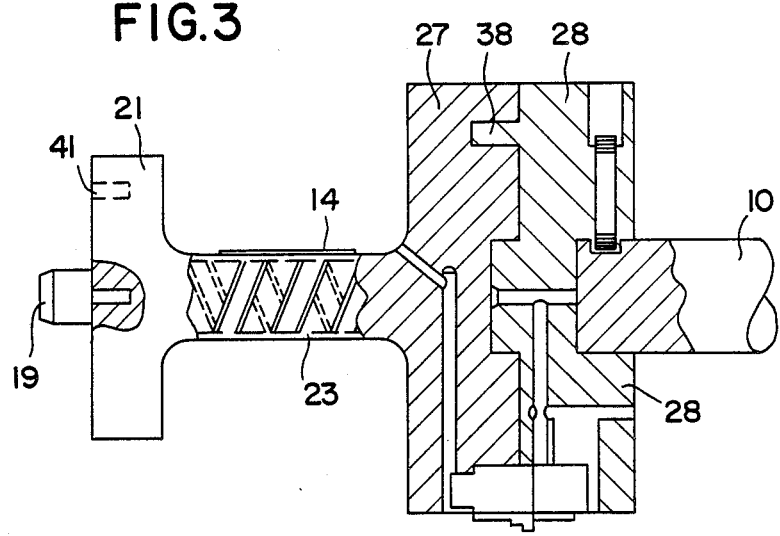
FIG. 3 is a cross-sectional partial break-away view of the decoupling interface of the shaft linkage.

With further regard to FIGS. 1 and 3, it is seen that the transducer 14 is electrically connected by wire 29, thru the power shaft 10, through slip rings 20, and to an output 22 of the system. This output is then fed to an analog-to-digital output for data processing.

Figure 4:
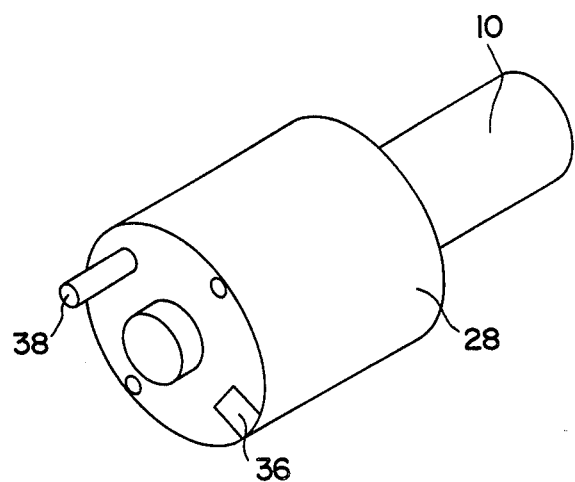
FIG. 4 is an isolated view of the female hub of the strain gauge shaft.

The central mechanical interface of the system is shown in FIGS. 3 and 4 in with linkage 23 is seen to connect to a male output hub 27 associated with the transducer 14 and its linkage 23. Therein, male hub 27 mates with female hub 28 through driving pin 38.

By the co-action of shear pin 40 and hole 41 (See FIG. 1), any torque overload developed in the operation of test chamber 12 will cause pin 40 to shear, thereby de-coupling the transducer from the test chamber at the interface between element 21 and driver coupling plate 42.

The present invention is to be understood as a method for testing the torque parameter repeatability of the test runs of a rheological measuring system.

In concept, the method comprises the step of using the torque transducer 14 to re-iteratively compare the integrated reactive torques imparted to said power shaft through the use of the respective rheological reference material samples and then comparing the reactive torques thereof. Thereby, differences in the comparative reactive torques measured by said torque transducer will indicate, if such is the case, any lack of repeatability in sequential test runs of the rheological measuring system. In effect, the present method of testing the output of the rheologic measuring instrument comprises a quality-control, calibration, and self-check means through which variations or floats in measurements from a microprocessor system can be ascertained before any production use of the material mixed within chamber 12 is made.

when viewed more particularly, the inventive method may be seen as comprising the steps of mechanically coupling said transducer 14, exteriorly of said test chamber 12, to a segment of a curved plane on the axis of rotation 16 of power shaft 10. Thereafter, test chamber 12 is filled with the sample material of a pre-defined quantity and rheological characteristic, while maintaining the same material at a pre-determined temperature. As a further step, the system is operated for a fixed duration. Thereafter, the output of transducer 14 is measured and recorded.

As a yet further step, test chamber 12 must be completely emptied and cleaned. Thereafter, and prior to the next contemplated test run of a formulation of said sample material, the said steps of operating the system for a fixed period of time, and measuring and recording the electrical output of said transducer are repeated. Thereafter, data generated by said repetition step and the first taking of the same data are compared. Thereby, differences in measurements recorded between the recorded torque outputs of the same rheologic reference standards will indicate the existence or absence of torque repeatability of the rheological measurement system. If lack of repeatability is found, there will, of course, be a need for recalibration of the test system. Further, external testing of the transducer is desirable for purposes of completeness.

Figure 2:
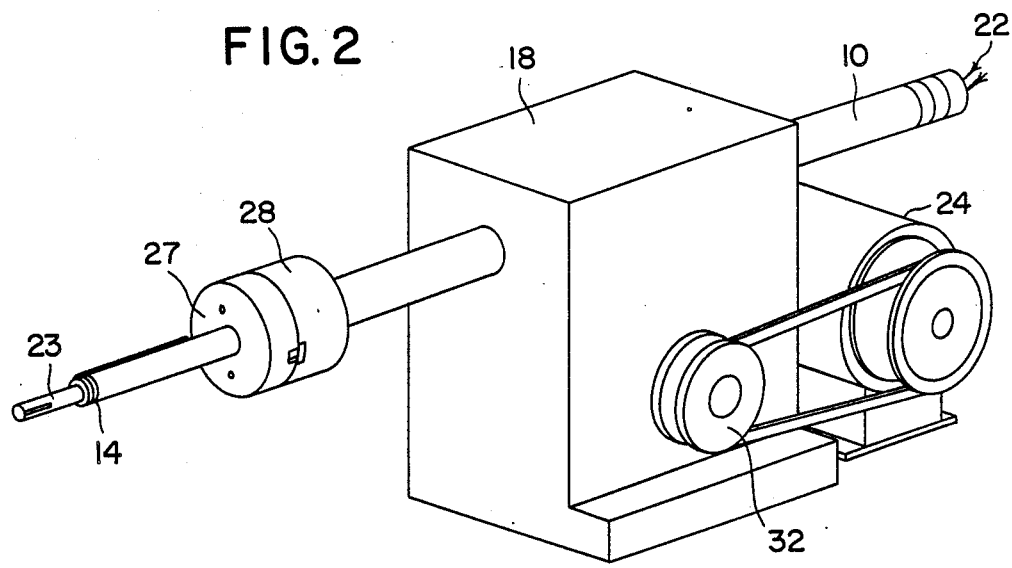
FIG. 2 is a perspective view of the exterior of the test system.

In FIG. 2, the rest of the system is shown schematically. This includes male and female hubs 27 and 28 which are operated by the gear box 18 which, in turn, is powered by right angle wormdrive 32 and AC motor 24.

While there has been herein shown and described the preferred embodiments of the present invention, it is to be understood the invention may be embodied otherwise than is herein illustrated and described and that in said embodiments, certain changes in the details of construction, and in the form and arrangement of parts may be made without departing from the underlying idea or principles of this invention within the scope of the appended Claims.

Having thus described our invention, what we claim as new, useful and nonobvious and, accordingly, secure by Letters Patent of the United States is:

1. A method for testing the torque-parameter repeatability of test runs of a rheological measuring system, said system having a power shaft and a test chamber, the method comprising the steps of:
   (a) providing a circumferential mixing element for said power shaft in said test chamber, said mixing element, when rotated, having a dynamic curvature;

(b) orienting a transducer within a spiral segment of a curved plane of rotation of said power shaft, said plane corresponding to the dynamic curvature of said mixing element of said power shaft, to reiteratively compare integrated axial and radial reactive torques imparted to said mixing element through the use of rheologic reference material samples for comparing the reactive torques thereof, whereby, reactive torques, both axial and radial, will be transmitted through the power shaft of said transducer and, further whereby, differences in the comparative reactive torques will indicate a lack of repeatability in sequential test runs of a measuring system.

2. The method as recited in claim 1, said providing step (a) more particularly comprising the step of:
   torsionally coupling said transducer to the axis of rotation of said power shaft.

3. The method as recited in claim 3 further comprising:
   the step of providing override means for de-coupling the power shaft in the event of mechanical or electrical overloads developed in operation of the test chamber.

4. The method as recited in claim 3, more particularly comprising the steps of:
   (c) filling of said test chamber with a material having a pre-defined quantity and rheologic characteristic, and maintaining said material at a pre-determined temperature;
   (d) operating the said system for a fixed period of time;
   (e) measuring and recording the electrical output of said strain transducer;
   (f) emptying and cleaning said test chamber of said system;
   (g) repeating said Steps (a) through (c) above; and
   (h) comparing the measurement data generated by said Steps (c) and (e) above, whereby differences in measurements of the reactive torque outputs of the said rheologic references samples will indicate any absence of repeatability in the system and, thereby, the need for a re-calibration of the test system.

5. A system for testing the repeatability of rheologic measurements, said system comprising:
   (a) a test chamber;
   (b) a power shaft extending into said test chamber;
   (c) a circumferential mixing element secured to said power shaft in said test chamber; and
   (d) a transducer oriented within a spiral segment of a curved plane of rotation of said power shaft, said plane of rotation corresponding to the dynamic curvature of said mixing element of said power shaft, said transducer secured to said power shaft outside of said mixing chamber, said transducer comprising means for the sensing of integrated axial and radial reactive torque transmitted from said mixing chamber through said power shaft to said transducer, said transducer further comprising means for re-iteratively comparing the integrated axial and radial reactive torque imparted to said mixing element through the reiterative use of rheologic reference material samples and the comparing of the reactive torques thereof, whereby differences in the comparative reactive torques measured by said torque transducer will indicate any lack of repeatability in the sequential outputs of a rheologic measuring system.

6. The system as recited in claim 6, in which said transducer is torsionally coupled to the axis rotation of said power shaft,
   whereby reactive torques, both axial and radial, from said mixing chamber will be transmitted through said power shaft to said transducer.

7. The system as recited in claim 6, further comprising:
   means for providing an override to de-couple said power shaft in the event of mechanical or electrical overloads developed in the operation of said test chamber.

* * * * *